US012656298B2

(12) United States Patent
Furuta et al.

(10) Patent No.: US 12,656,298 B2
(45) Date of Patent: Jun. 16, 2026

(54) GAS SENSOR ELEMENT, GAS SENSOR, AND MANUFACTURING METHOD FOR GAS SENSOR ELEMENT

(71) Applicant: NITERRA CO., LTD., Nagoya (JP)

(72) Inventors: Hitoshi Furuta, Nagoya (JP); Kei Yoshikawa, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 385 days.

(21) Appl. No.: 18/500,237

(22) Filed: Nov. 2, 2023

(65) Prior Publication Data

US 2024/0151684 A1 May 9, 2024

(30) Foreign Application Priority Data

Nov. 8, 2022 (JP) ................................. 2022-178616

(51) Int. Cl.
*G01N 27/407* (2006.01)
*G01N 27/41* (2006.01)
*G01N 33/00* (2006.01)

(52) U.S. Cl.
CPC ......... *G01N 27/4071* (2013.01); *G01N 27/41* (2013.01); *G01N 33/0027* (2013.01)

(58) Field of Classification Search
CPC .. G01N 27/4071; G01N 27/41; G01N 27/417; G01N 27/4072; G01N 27/4074; G01N 33/0027
See application file for complete search history.

(56) References Cited

U.S. PATENT DOCUMENTS

2012/0217160 A1* 8/2012 Hayashi ............. G01N 27/4071
204/424
2013/0019655 A1* 1/2013 Nakagawa ........... G01N 27/419
73/31.05

2015/0219591 A1* 8/2015 Shimizu ............. G01N 27/4073
204/426
2019/0277796 A1* 9/2019 Kamada ............... G01N 27/409
2019/0360961 A1* 11/2019 Yamada ............. G01N 33/0054
2021/0080423 A1* 3/2021 Furuta ................ G01N 27/4074

FOREIGN PATENT DOCUMENTS

JP 2017211186 A * 11/2017
JP 2021-51058 A 4/2021

OTHER PUBLICATIONS

Igarashi et al., JP2017211186A, English translation, 2017 (Year: 2017).*

* cited by examiner

*Primary Examiner* — Shizhi Qian
(74) *Attorney, Agent, or Firm* — Stites & Harbison, PLLC; Jeffrey A. Haeberlin

(57) ABSTRACT

A gas sensor element includes: a second ceramic layer including a pump cell in which a first electrode and a second electrode are provided on a surface of a first solid electrolyte body; a first ceramic layer including a measurement chamber which is faced by the first electrode and into which a gas to be measured flows; a porous body covering the second electrode; and a dense layer having a void and not allowing the gas to be measured to pass therethrough. The second electrode and the void are connected through the porous body. A reinforcing layer which is porous and contains, as a main component, a component having a lower firing start temperature than a main component of the porous body is interposed between the second electrode and the porous body at a position overlapping the void in a thickness direction of the porous body.

6 Claims, 5 Drawing Sheets

GAS SENSOR ELEMENT, GAS SENSOR, AND MANUFACTURING METHOD FOR GAS SENSOR ELEMENT

TECHNICAL FIELD

The technology disclosed herein relates to a gas sensor element, a gas sensor, and a manufacturing method for a gas sensor element.

BACKGROUND ART

As a gas sensor for measuring the concentration of a specific component in exhaust gas from an internal combustion engine, for example, a gas sensor described in Japanese Patent Application Laid-Open (kokai) No. 2021-51058 (Patent Document 1 below) is known. This gas sensor includes a sensor element composed mainly of ceramic. Inside the sensor element, a first measurement chamber used as a measurement chamber, a void for introducing atmospheric air serving as reference gas into the inside, and an Ip1 cell placed between the first measurement chamber and the void and including a solid electrolyte body and a pair of electrodes, are provided. A porous layer that allows atmospheric air to pass therethrough is placed on the surface of each electrode. Such a sensor element is formed by laminating a plurality of ceramic green sheets and then firing the ceramic green sheets.

PRIOR ART DOCUMENT

Patent Document

[Patent Document 1] Japanese Patent Application Laid-Open (kokai) No. 2021-51058

SUMMARY OF THE INVENTION

Problems to be Solved by the Invention

In the sensor element having the above configuration, the solid electrolyte body may warp so as to project toward the first measurement chamber side during firing, causing cracks, and improvement has been required.

Means for Solving the Problems

A gas sensor element disclosed herein is a gas sensor element including: a second ceramic layer including a pump cell in which a first electrode and a second electrode are provided on a surface of a solid electrolyte body; a first ceramic layer including a measurement chamber which is faced by the first electrode and into which a gas to be measured flows; a porous body covering the second electrode; and a dense layer having a void and not allowing the gas to be measured to pass therethrough, wherein the second electrode and the void are connected through the porous body, and a reinforcing layer which is porous and contains, as a main component, a component having a lower sintering start temperature than a main component of the porous body is interposed between the second electrode and the porous body at a position overlapping the void in a thickness direction of the porous body.

A gas sensor disclosed herein includes the above gas sensor element.

A manufacturing method for a gas sensor element disclosed herein is a manufacturing method for a gas sensor element including: a second ceramic layer including a pump cell in which a first electrode and a second electrode are provided on a surface of a solid electrolyte body; a first ceramic layer including a measurement chamber which is faced by the first electrode and into which a gas to be measured flows; a porous body covering the second electrode; and a dense layer having a void and not allowing the gas to be measured to pass therethrough, the second electrode and the void being connected through the porous body, the manufacturing method including a lamination step of forming an unfired laminate which is the gas sensor element before firing, and a firing step of firing the unfired laminate to produce the gas sensor element, after the lamination step, wherein, in the gas sensor element, a reinforcing layer which is porous and contains, as a main component, a component having a lower sintering start temperature than a main component of the porous body is interposed between the second electrode and the porous body at a position overlapping the void in a thickness direction of the porous body, and the lamination step includes filling a region which becomes the void after firing, in the unfired dense layer, with a vanishing material which vanishes due to firing, and forming an unfired reinforcing layer between an unfired second electrode and an unfired porous body.

Effects of the Invention

With the gas sensor element, the gas sensor, and the manufacturing method for the gas sensor element disclosed herein, occurrence of cracks around the space which becomes the measurement chamber can be suppressed.

DETAILED DESCRIPTION OF EXEMPLARY EMBODIMENTS OF THE INVENTION

Summary of Embodiments

Figure 1:
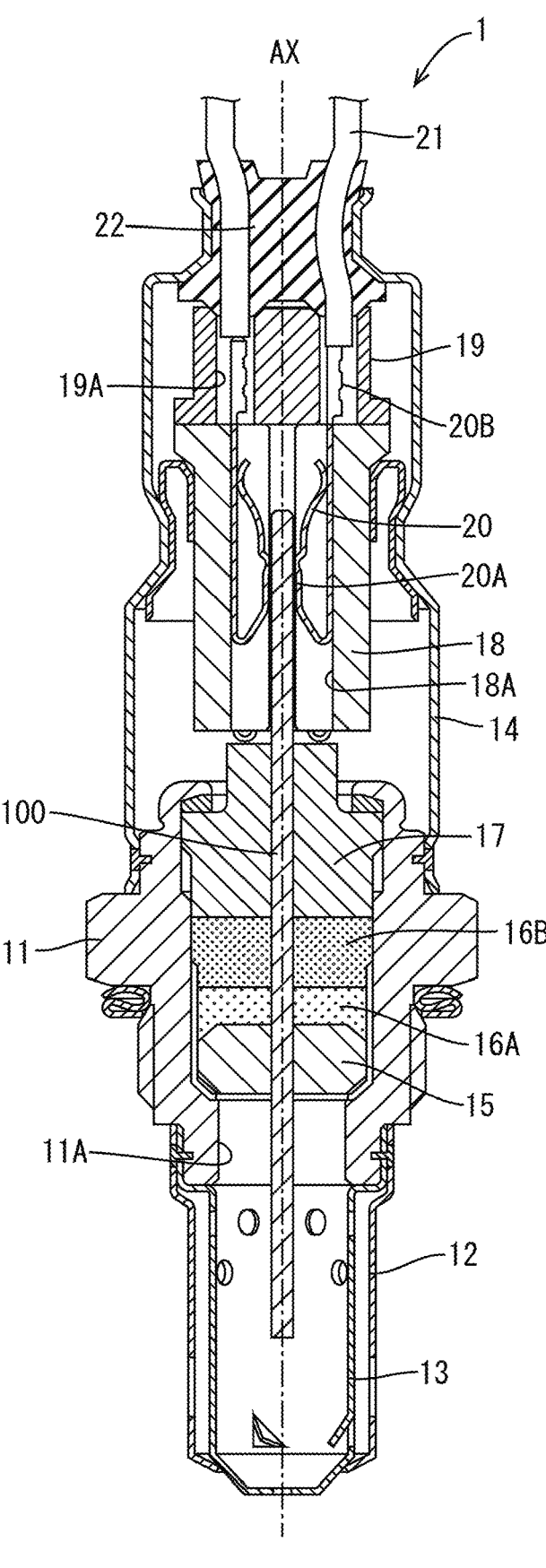
FIG. 1 is a cross-sectional view of a gas sensor of an embodiment.

A gas sensor element disclosed herein is a gas sensor element including: a second ceramic layer including a pump cell in which a first electrode and a second electrode are provided on a surface of a solid electrolyte body; a first ceramic layer including a measurement chamber which is faced by the first electrode and into which a gas to be measured flows; a porous body covering the second electrode; and a dense layer having a void and not allowing the gas to be measured to pass therethrough, wherein the second electrode and the void are connected through the porous body, and a reinforcing layer which is porous and contains, as a main component, a component having a lower sintering start temperature than a main component of the porous body is interposed between the second electrode and the porous body at a position overlapping the void in a thickness direction of the porous body.

A gas sensor disclosed herein includes the above gas sensor element.

A manufacturing method for a gas sensor element disclosed herein is a manufacturing method for a gas sensor element including: a second ceramic layer including a pump cell in which a first electrode and a second electrode are provided on a surface of a solid electrolyte body; a first ceramic layer including a measurement chamber which is faced by the first electrode and into which a gas to be measured flows; a porous body covering the second electrode; and a dense layer having a void and not allowing the gas to be measured to pass therethrough, the second electrode and the void being connected through the porous body, the manufacturing method including a lamination step of forming an unfired laminate which is the gas sensor element before firing, and a firing step of firing the unfired laminate to produce the gas sensor element, after the lamination step, wherein, in the gas sensor element, a reinforcing layer which is porous and contains, as a main component, a component having a lower sintering start temperature than a main component of the porous body is interposed between the second electrode and the porous body at a position overlapping the void in a thickness direction of the porous body, and the lamination step includes filling a region which becomes the void after firing, in the unfired dense layer, with a vanishing material which vanishes due to firing, and forming an unfired reinforcing layer between an unfired second electrode and an unfired porous body. Here, the unfired dense layer is the dense layer before firing, the unfired porous body is the porous body before firing, and the unfired reinforcing layer is the reinforcing layer before firing.

The cracks around the measurement chamber are considered to be caused by the second ceramic layer warping so as to project toward the measurement chamber side during firing. Since the reinforcing layer having a lower sintering start temperature than the porous body is interposed between the second electrode and the porous body, and sintering of the reinforcing layer is started earlier than the second ceramic layer during firing, the warp of the second ceramic layer can be alleviated, so that occurrence of cracks can be suppressed.

In the gas sensor element or the gas sensor in the above, the reinforcing layer may contain zirconia as a main component.

In the gas sensor element or the gas sensor in the above, the reinforcing layer may be placed so as to overlap a measurement chamber arrangement region in which the measurement chamber is arranged, as viewed in a thickness direction of the first ceramic layer.

In the second ceramic layer, the portion overlapping the measurement chamber arrangement region is likely to warp. Since the reinforcing layer is placed at the position overlapping the measurement chamber arrangement region, occurrence of cracks can be more effectively suppressed.

In the gas sensor element or the gas sensor in any one of the above, the reinforcing layer may have an outer shape larger than the measurement chamber arrangement region and may overlap the entire measurement chamber arrangement region.

With such a configuration, even if some misalignment of the reinforcing layer occurs during the manufacturing of the gas sensor element, occurrence of cracks can be suppressed.

Details of Embodiments

Specific examples of the technology disclosed herein will be described below with reference to FIG. 1 to FIG. 5. The present invention is not limited to these examples, is indicated by the claims, and is intended to include all modifications within the meaning and scope equivalent to the claims.

Entire Configuration of Gas Sensor 1

A gas sensor 1 of an embodiment is a NOx sensor that is installed in a flow path of exhaust gas discharged from an engine (internal combustion engine) in a vehicle and that is used for measuring the concentration of nitrogen oxides contained in the exhaust gas.

As shown in FIG. 1, the gas sensor 1 includes a gas sensor element 100, a metal shell 11, an external protector 12, an internal protector 13, an outer casing 14, a holding member 18, an insulating member 19, and a plurality of (six in the present embodiment) terminal members 20. The gas sensor element 100 has an elongated plate shape extending in an axial line AX direction (up-down direction in FIG. 1), and is held inside the metal shell 11. In the following description, the lower side in FIG. 1 is referred to as front end side, and the upper side in FIG. 1 is referred to as rear end side.

The metal shell 11 is a tubular member having a through hole 11A which penetrates the member in the axial line AX direction. The metal shell 11 holds the gas sensor element 100 inside the through hole 11A in a state where a front end portion of the gas sensor element 100 projects to the outside on the front end side of the metal shell 11 and a rear end portion of the gas sensor element 100 projects to the outside on the rear end side of the metal shell 11.

Inside the through hole 11A of the metal shell 11, an annular ceramic holder 15, two talc rings 16A and 16B formed by annularly filling this hole with talc powder, and a ceramic sleeve 17 are placed. Specifically, the ceramic holder 15, the talc rings 16A and 16B, and the ceramic sleeve 17 are placed in an overlapping manner in this order from the front end side to the rear end side of the metal shell 11 so as to surround the gas sensor element 100.

The external protector 12 and the internal protector 13 which are made of metal are attached to a front end portion of the metal shell 11 by welding. The internal protector 13 has a tubular shape extending in the axial line AX direction, and surrounds the front end portion of the gas sensor element 100. The external protector 12 has a tubular shape extending in the axial line AX direction, and surrounds the internal protector 13. The external protector 12 and the internal protector 13 each have a plurality of holes. The outer casing 14 is attached to a rear end portion of the metal shell 11 by welding. The outer casing 14 has a tubular shape extending in the axial line AX direction, and surrounds the rear end portion of the gas sensor element 100.

Inside the outer casing 14, the holding member 18 and the insulating member 19 are placed in this order from the front end side. The holding member 18 is a tubular member made of an insulating material (specifically, alumina) and having an insertion hole 18A which penetrates the member in the axial line AX direction. The rear end portion of the gas sensor element 100 is placed inside the insertion hole 18A. The insulating member 19 is made of an insulating material (specifically, alumina) and has a plurality of through holes 19A which penetrate the insulating member 19 in the axial line AX direction.

Each terminal member 20 is made of a conductive material such as metal, and includes an element contact portion 20A and a lead connection portion 20B connected to the element contact portion 20A. The element contact portion 20A is placed inside the insertion hole 18A and is in contact with the gas sensor element 100. The lead connection portion 20B is placed inside each of the plurality of through holes 19A, and is connected to a terminal portion of a lead wire 21. FIG. 1 illustrates two of the six terminal members 20.

An elastic seal member 22 made of a fluororubber is placed in the opening on the rear end side of the outer casing 14. A plurality of lead wires 21 connected to the plurality of terminal members 20 are led out through the elastic seal member 22.

Configuration of Gas Sensor Element 100

Figure 3:
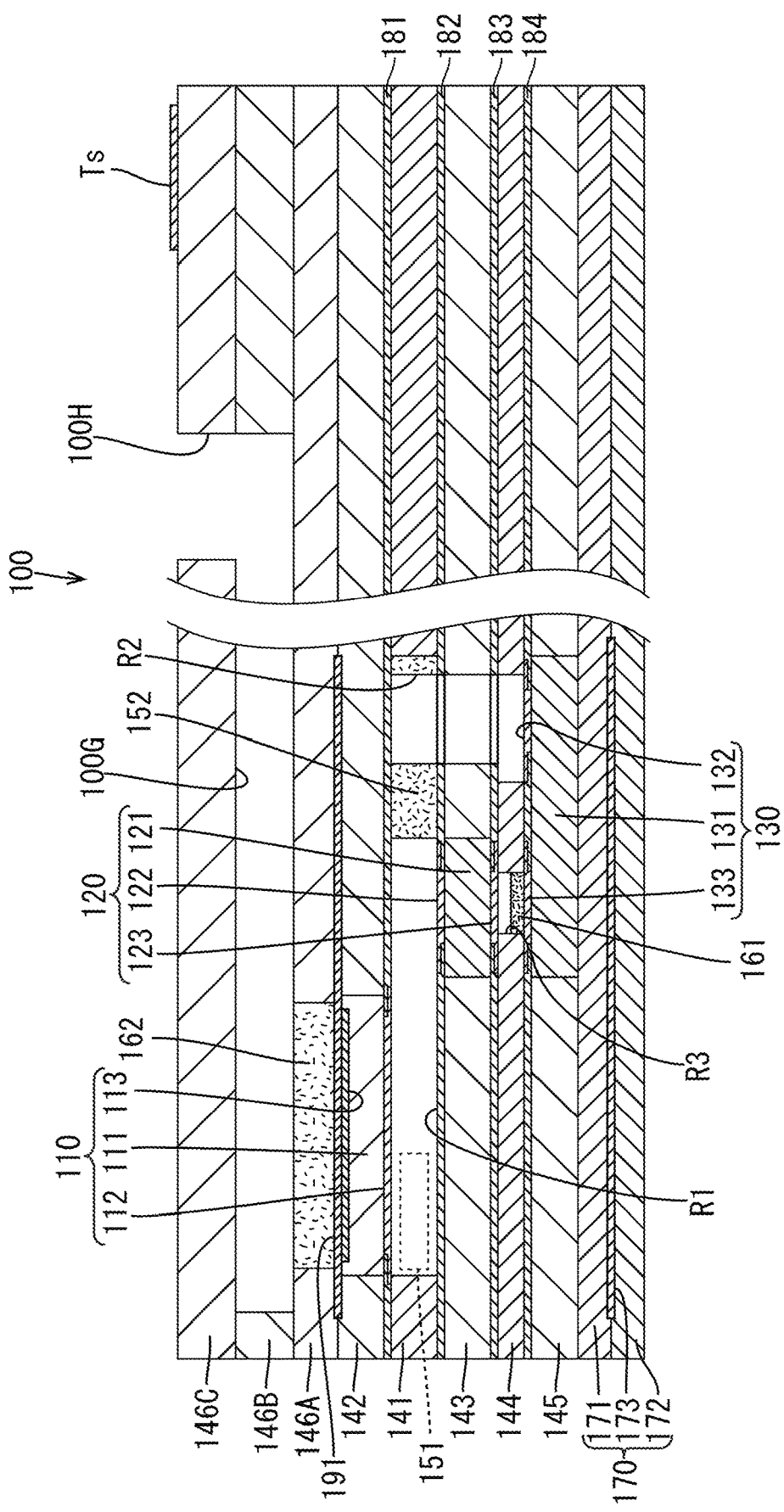
FIG. 3 is a cross-sectional view taken along a line A-A in FIG. 2.

As shown in FIG. 3, the gas sensor element 100 includes a pump cell 110, a Vs cell 120, a detection cell 130, a first measurement chamber R1, a second measurement chamber R2, a reference oxygen chamber R3, and a heater 170.

Figure 4:
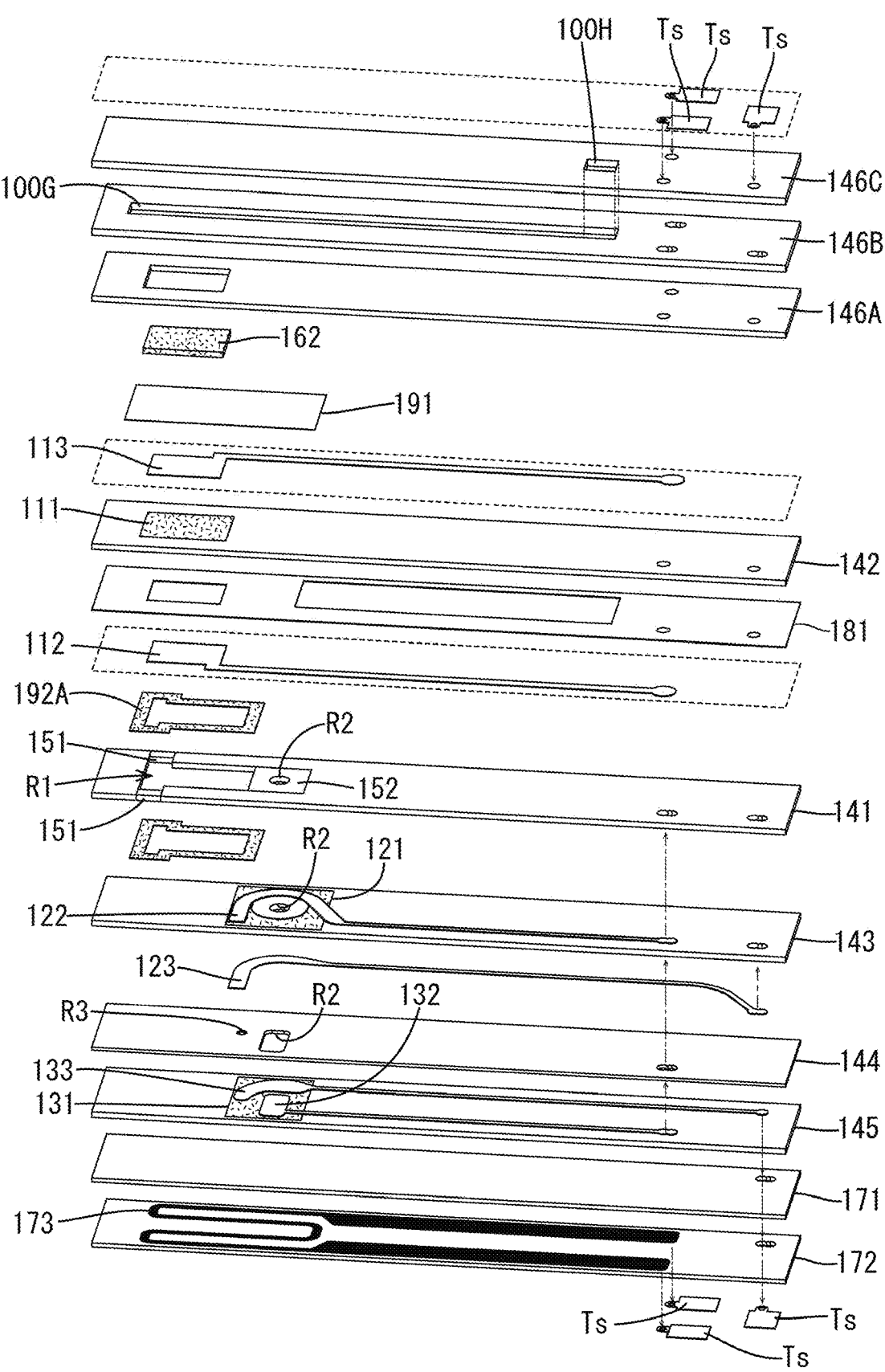
FIG. 4 is an exploded perspective view of a gas sensor element of the embodiment.

As shown in FIG. 3 and FIG. 4, the gas sensor element 100 has a structure in which a third dense layer 146C, a second dense layer 146B, a first dense layer 146A, a second insulating layer 142, a first insulating layer 141, a third insulating layer 143, a fourth insulating layer 144, a fifth insulating layer 145, a sixth insulating layer 171, and a seventh insulating layer 172 are laminated in this order. A first solid electrolyte body 111 is formed in the second insulating layer 142. A second solid electrolyte body 121 is formed in the third insulating layer 143. A third solid electrolyte body 131 is formed in the fifth insulating layer 145.

The first measurement chamber R1 is a small space that is provided between a layer composed of the second insulating layer 142 and the first solid electrolyte body 111 and a layer composed of the third insulating layer 143 and the second solid electrolyte body 121 and that penetrates the first insulating layer 141. The first measurement chamber R1 is separated from the outer space by a first diffusion resistance body 151 which allows gas to pass therethrough. The first diffusion resistance body 151 limits the flowing amount of exhaust gas from the outside to the first measurement chamber R1 per unit time.

The second measurement chamber R2 is a small space provided between the layer composed of the second insulating layer 142 and the first solid electrolyte body 111 and a layer composed of the fifth insulating layer 145 and the third solid electrolyte body 131, and penetrates the first insulating layer 141, the third insulating layer 143, and the fourth insulating layer 144. The first measurement chamber R1 and the second measurement chamber R2 are separated from each other by a second diffusion resistance body 152 which allows gas to pass therethrough. The second diffusion resistance body 152 limits the flowing amount of exhaust gas from the first measurement chamber R1 to the second measurement chamber R2 per unit time.

The reference oxygen chamber R3 is a small space provided between the layer composed of the third insulating layer 143 and the second solid electrolyte body 121 and the layer composed of the fifth insulating layer 145 and the third solid electrolyte body 131, and penetrates the fourth insulating layer 144. A first porous body 161 which allows gas to pass therethrough is placed inside the reference oxygen chamber R3.

The second dense layer 146B has an atmospheric air introduction space 100G. The atmospheric air introduction space 100G is a small space that is provided between the first dense layer 146A and the third dense layer 146C and that penetrates the second dense layer 146B. The third dense layer 146C has an atmospheric air introduction port 100H which provides communication between the atmospheric air introduction space 100G and the outer space of the gas sensor element 100. Atmospheric air serving as a reference gas is introduced into the atmospheric air introduction space 100G through the atmospheric air introduction port 100H. A second porous body 162 which is porous and allows the atmospheric air to pass therethrough is formed in the first dense layer 146A.

The insulating layers 141, 142, 143, 144, 145, 146A, 146B, 146C, 171, and 172 are dense layers containing alumina as a main component. The porous bodies 161 and 162 and the diffusion resistance bodies 151 and 152 are porous bodies containing alumina as a main component. The solid electrolyte bodies 111, 121, and 131 contain zirconia, which has oxygen ion conductivity, as a main component. In the present embodiment, the main component means that the content thereof is not less than 50 mass %.

A first reinforcing layer 191 is interposed between the first dense layer 146A and the second insulating layer 142. The entire first reinforcing layer 191 is embedded inside the gas sensor element 100. The first reinforcing layer 191 is a porous body that allows atmospheric air to pass therethrough, and one surface (upper surface in FIG. 3) thereof is in contact with the second porous body 162. The first reinforcing layer 191 contains, as a main component, a component (zirconia in the present embodiment) having a lower shrinkage start temperature than the main component of the second porous body 162 (alumina in the present embodiment). The first reinforcing layer 191 is porous.

Figure 2:
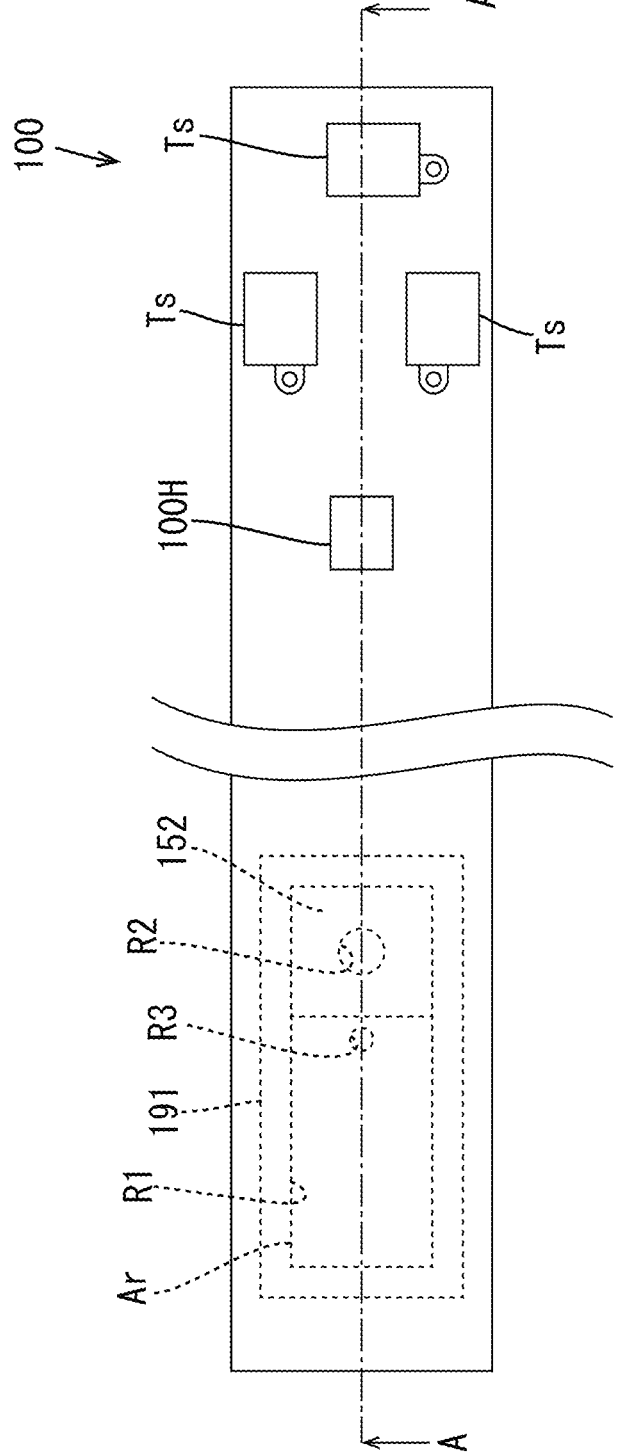
FIG. 2 is a side view of the gas sensor element of the embodiment as viewed in a direction perpendicular to a first insulating layer.

The first reinforcing layer 191 has an outer shape larger than a measurement chamber arrangement region Ar in which the measurement chambers R1 and R2 are arranged, as viewed in a direction perpendicular to the first insulating layer 141 (thickness direction of the first insulating layer 141 in FIG. 3), and is placed so as to overlap the entire measurement chamber arrangement region Ar (see FIG. 2). In the case where the gas sensor element 100 has a plurality of measurement chambers R1 and R2 as in the present embodiment, the measurement chamber arrangement region Ar is a region covering all of the plurality of measurement chambers R1 and R2 as viewed in the direction perpendicular to the first insulating layer 141.

The pump cell 110 includes the first solid electrolyte body 111, a first electrode 112 placed on a surface (lower surface in FIG. 3) of the first solid electrolyte body 111, and a second electrode 113 placed on another surface (upper surface in FIG. 3) of the first solid electrolyte body 111 and paired with the first electrode 112. The first electrode 112 is placed so as to face the first measurement chamber R1. The second electrode 113 is placed outside the first measurement chamber R1, and is in contact with a surface (lower surface in FIG. 3) of the first reinforcing layer 191 opposite to the surface of the first reinforcing layer 191 that is in contact with the second porous body 162. That is, the first reinforcing layer 191 is interposed between the second electrode 113 and the second porous body 162.

The Vs cell 120 includes the second solid electrolyte body 121, a third electrode 122 placed on a surface (upper surface in FIG. 3) of the second solid electrolyte body 121, and a fourth electrode 123 placed on another surface (lower surface in FIG. 3) of the second solid electrolyte body 121 and paired with the third electrode 122. The third electrode 122 is placed so as to face the first measurement chamber R1. The fourth electrode 123 is placed so as to face the reference oxygen chamber R3.

The detection cell 130 includes the third solid electrolyte body 131, a fifth electrode 132 placed on a surface (upper surface in FIG. 3) of the third solid electrolyte body 131, and a sixth electrode 133 placed on the surface (upper surface in FIG. 3) of the third solid electrolyte body 131 and paired with the fifth electrode 132. The fifth electrode 132 is placed so as to face the second measurement chamber R2. The sixth electrode 133 is placed so as to face the reference oxygen chamber R3 and oppose the fourth electrode 123.

The first electrode 112, the third electrode 122, and the fifth electrode 132 are each connected to a reference potential.

An alumina insulating layer 181 is placed between the first insulating layer 141 and the second insulating layer 142 at a position excluding the first electrode 112. Alumina insulating layers 182, 183, and 184 are interposed between the first insulating layer 141 and the third insulating layer 143, between the third insulating layer 143 and the fourth insulating layer 144, and between the fourth insulating layer 144 and the fifth insulating layer 145, respectively, at positions excluding the electrodes 122, 123, 132, and 133 and the second measurement chamber R2. For ease of viewing the drawing, the alumina insulating layers 182, 183, and 184 are not shown in FIG. 4.

Second reinforcing layers 192A and 192B are placed between the alumina insulating layer 181 and the first insulating layer 141 and between the first insulating layer 141 and the third insulating layer 143 along the opening edge of the first measurement chamber R1. Third reinforcing layers (not shown) are placed between the third dense layer 146C and the second dense layer 146B and between the second dense layer 146B and the first dense layer 146A along the opening edge of the atmospheric air introduction space 100G. The second reinforcing layers 192A and 192B and the third reinforcing layers contain zirconia as a main component as in the first reinforcing layer 191. For ease of viewing the drawing, the second reinforcing layers 192A and 192B and the third reinforcing layers are not shown in FIG. 3. Although not shown in detail, a reinforcing layer containing zirconia as a main component is also placed at an end portion of a surface (lower surface in FIG. 3), of the third insulating layer 143, facing the fourth insulating layer 144.

The heater 170 includes the sixth insulating layer 171, the seventh insulating layer 172, and a resistance heating element 173 which is embedded between the sixth insulating layer 171 and the seventh insulating layer 172 and which generates heat when energized. The heater 170 is used to heat the solid electrolyte bodies 111, 121, and 131 to a temperature at which the solid electrolyte bodies 111, 121, and 131 become activated, and to increase the oxygen ion conductivity of the solid electrolyte bodies 111, 121, and 131 to stabilize the operation.

The electrodes 112, 113, 122, 123, 132, and 133 and the resistance heating element 173 contain platinum as a main component.

Six electrode terminal portions Ts are placed on the surface of the gas sensor element 100 so as to be electrically connected to the six electrodes 112, 113, 122, 123, 132, and 133, respectively, by leads and through holes. The element contact portions 20A of the six terminal members 20 are in elastic contact with the six electrode terminal portions Ts, respectively.

Operation of Gas Sensor 1

A process of measuring nitrogen oxides in exhaust gas of a vehicle by the above gas sensor 1 will be briefly described.

When the engine of the vehicle is started and a drive current is applied to the resistance heating element 173, the temperature of the resistance heating element 173 rises, and the solid electrolyte bodies 111, 121, and 131 are heated and activated. Accordingly, the pump cell 110, the Vs cell 120, and the detection cell 130 operate.

The exhaust gas enters the first measurement chamber R1 with the flowing amount thereof being limited by the first diffusion resistance body 151. At this time, a weak current Ip1 is applied to the Vs cell 120 so as to flow from the fourth electrode 123 to the third electrode 122. Accordingly, oxygen in the exhaust gas inside the first measurement chamber R1 can receive electrons from the third electrode 122 which becomes a negative electrode, flows in the second solid electrolyte body 121 as oxygen ions, and moves into the reference oxygen chamber R3. That is, the oxygen inside the first measurement chamber R1 is sent into the reference oxygen chamber R3.

If the oxygen concentration of the exhaust gas inside the first measurement chamber R1 is lower than a predetermined value, the current Ip1 is applied to the pump cell 110 such that the second electrode 113 becomes a negative electrode, and oxygen is pumped into the first measurement chamber R1 from the outside. On the other hand, if the oxygen concentration of the exhaust gas introduced into the first measurement chamber R1 is higher than the predetermined value, the current Ip1 is applied to the pump cell 110 such that the first electrode 112 becomes a negative electrode, and oxygen is pumped from the inside of the first measurement chamber R1 to the outside.

The exhaust gas whose oxygen concentration has been adjusted in the first measurement chamber R1 enters the second measurement chamber R2 with the flowing amount thereof being limited by the second diffusion resistance body 152. The nitrogen oxides in the exhaust gas which contacts with the fifth electrode 132 inside the second measurement chamber R2 is decomposed to nitrogen and oxygen on the fifth electrode 132 by applying a voltage Vp2 between the fifth electrode 132 and the sixth electrode 133. The oxygen resulting from the decomposition flows in the third solid electrolyte body 131 as oxygen ions and moves into the reference oxygen chamber R3. At this time, a current Ip2 flowing in the detection cell 130 indicates a value corresponding to the nitrogen oxide concentration, and thus the nitrogen oxide concentration of the exhaust gas can be known on the basis of the current value.

Manufacturing Method for Gas Sensor Element 100

Figure 5:
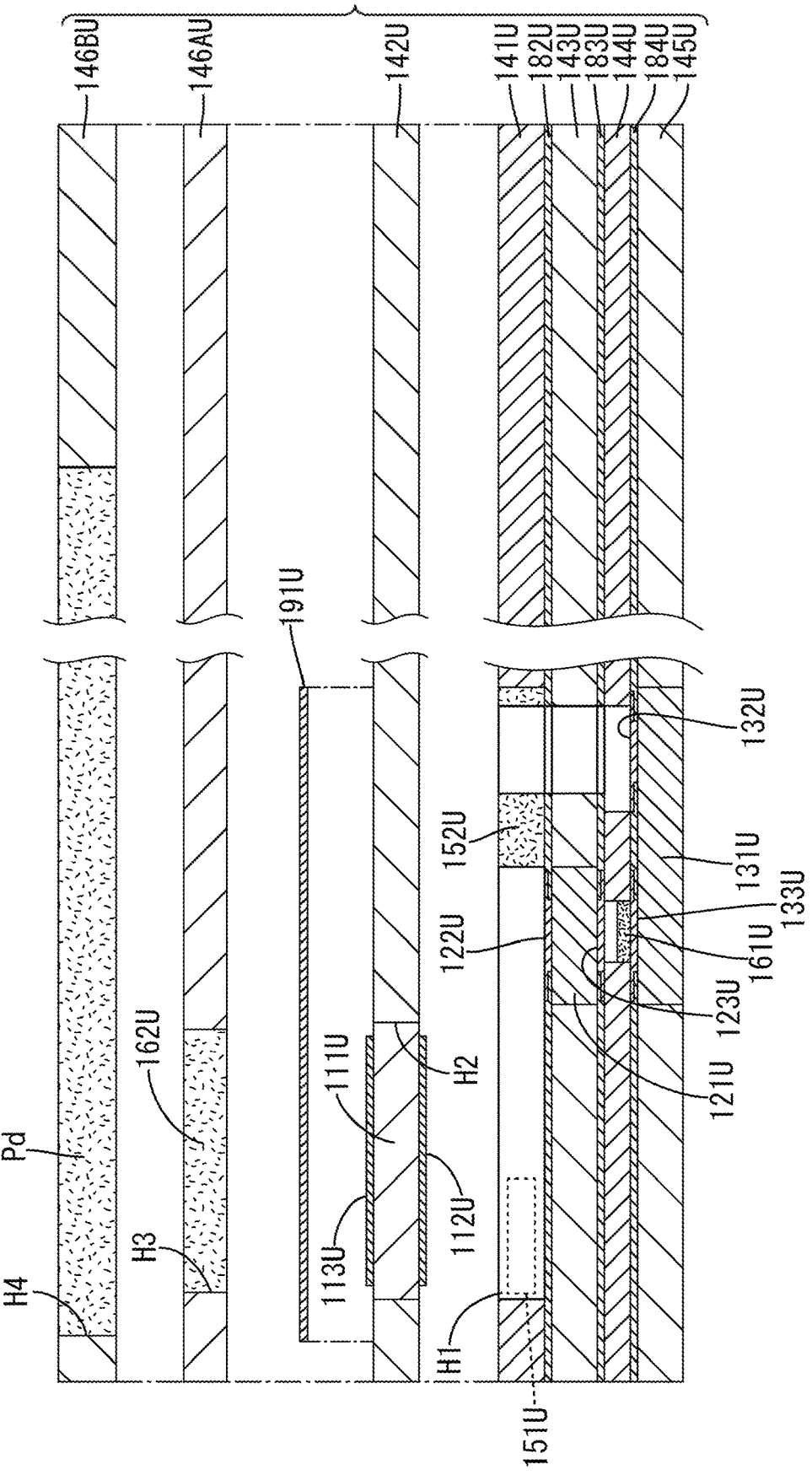
FIG. 5 is a cross-sectional view showing a state in the middle of manufacturing of the gas sensor element of the embodiment.

Next, an example of a method for manufacturing the gas sensor element 100 having the above configuration will be described with reference to FIG. 5.

First, an unfired laminate L which is the gas sensor element 100 before firing is produced (lamination step). The unfired laminate L is a laminate including, in order from below, an unfired fifth ceramic layer 145U which becomes the fifth insulating layer 145 after firing, an unfired fourth ceramic layer 144U which becomes the fourth insulating layer 144 after firing, an unfired third ceramic layer 143U which becomes the third insulating layer 143 after firing, an unfired first ceramic layer 141U which becomes the first insulating layer 141 after firing, an unfired second ceramic layer 142U which becomes the second insulating layer 142 after firing, an unfired dense layer 146AU which becomes the first dense layer 146A after firing, and an unfired dense layer 146BU which becomes the second dense layer 146B after firing. An unfired third solid electrolyte body 131U which becomes the third solid electrolyte body 131 after firing is formed in the unfired fifth ceramic layer 145U, and an unfired fifth electrode 132U which becomes the fifth electrode 132 after firing and an unfired sixth electrode 133U which becomes the sixth electrode 133 after firing are formed on the surface of the unfired third solid electrolyte body 131U. On the unfired fifth ceramic layer 145U, the unfired fourth ceramic layer 144U and the unfired third ceramic layer 143U are formed sequentially with unfired insulating layers 183U and 184U, which become the alumina insulating layers 183 and 184 after firing, being interposed therebetween. In the unfired fourth ceramic layer 144U, an unfired first porous body 161U which becomes the first porous body 161 after firing is formed at a position at which the reference oxygen chamber R3 is to be formed. An unfired second solid electrolyte body 121U which becomes the second solid electrolyte body 121 after firing is formed in the unfired third ceramic layer 143U, and an unfired third electrode 122U and an unfired fourth electrode 123U which become the third electrode 122 and the fourth electrode 123 after firing are formed on the surface of the unfired second solid electrolyte body 121U.

Next, the unfired first ceramic layer 141U is formed on the unfired third ceramic layer 143U with an unfired insulating layer 182U, which becomes the alumina insulating layer 182 after firing, being interposed therebetween. In the unfired first ceramic layer 141U, a first through hole H1 is formed so as to penetrate the unfired first ceramic layer 141U in the thickness direction, and an unfired first diffusion resistance body 151U which becomes the first diffusion resistance body 151 after firing is formed inside the first through hole H1.

In the unfired second ceramic layer 142U, a second through hole H2 is formed so as to penetrate the unfired second ceramic layer 142U, and an unfired first solid electrolyte body 111U which becomes the first solid electrolyte body 111 after firing is formed inside the second through hole H2. Then, an unfired first electrode 112U which becomes the first electrode 112 after firing is formed on one surface of the unfired first solid electrolyte body 111U, and an unfired second electrode 113U which becomes the second electrode 113 after firing is formed on another surface of the unfired first solid electrolyte body 111U.

In the unfired dense layer 146AU, a third through hole H3 is formed so as to penetrate the unfired dense layer 146AU, and an unfired second porous body 162U which becomes the second porous body 162 after firing is embedded inside the third through hole H3. The unfired second porous body 162U is, for example, a sheet containing a first ceramic material composed of ceramics and a vanishing material which vanishes due to firing. The first ceramic material is, for example, alumina powder, and the vanishing material is, for example, carbon powder.

In the unfired dense layer 146BU, a fourth through hole H4 which becomes the atmospheric air introduction space 100G is formed so as to penetrate the unfired dense layer 146BU, and the interior of the fourth through hole H4 is filled with a vanishing paste Pd containing a vanishing material which vanishes due to firing. The vanishing material is, for example, carbon powder.

An unfired reinforcing layer 191U containing a ceramic material and a vanishing material which vanishes due to firing and having a lower shrinkage start temperature than the unfired second porous body 162U is formed on the surface of the unfired second ceramic layer 142U so as to cover the unfired second electrode 113U.

Another unfired dense layer and unfired ceramic layers which become the third dense layer 146C, the sixth insulating layer 171, and the seventh insulating layer 172 are formed, and portions which become the resistance heating element 173 and the atmospheric air introduction port 100H are formed in these unfired dense layer and unfired ceramic layers. For ease of viewing the drawing, these unfired dense layer and unfired ceramic layers are not shown in FIG. 5. Thus, the unfired laminate L is formed.

After the lamination step, the unfired laminate L is fired to produce the gas sensor element 100 (firing step).

In the obtained gas sensor element 100, cracks may have occurred around the space which becomes the first measurement chamber R1. When the gas sensor element 100 is observed, it has been found that the second insulating layer 142 warps so as to project toward the first measurement chamber R1 side, and the first measurement chamber R1 side is the starting point of the cracks. From this, it is inferred that tensile stress is generated at the interface on the first measurement chamber R1 side in the second insulating layer 142. In the present embodiment, the unfired reinforcing layer 191U having a lower shrinkage start temperature than the unfired second porous body 162U is interposed between the unfired second electrode 113U which becomes the second electrode 113 and the unfired second porous body 162U which becomes the second porous body 162, and this unfired reinforcing layer 191U is caused to shrink earlier than the unfired second porous body 162U during firing, thereby alleviating the tensile stress generated at the interface on the first measurement chamber R1 side in the second insulating layer 142. Accordingly, the warp of the second insulating layer 142 can be alleviated, so that occurrence of cracks can be suppressed.

Effects

As described above, according to the present embodiment, the gas sensor element 100 includes: the second insulating layer 142 including the pump cell 110 in which the first electrode 112 and the second electrode 113 are provided on the surface of the first solid electrolyte body 111; the first insulating layer 141 including the first measurement chamber R1 which is faced by the first electrode 112 and into which a gas to be measured flows; the second porous body 162 covering the second electrode 113; and the dense layers 146A, 146B, and 146C having the atmospheric air introduction space 100G and not allowing the gas to be measured to pass therethrough, wherein the second electrode 113 and the atmospheric air introduction space 100G are connected through the second porous body 162, and the first reinforcing layer 191 which is porous and contains, as a main component, a component having a lower sintering start temperature than the main component of the second porous body 162 is interposed between the second electrode 113 and the second porous body 162 at a position overlapping the atmospheric air introduction space 100G in the thickness direction of the second porous body 162.

A manufacturing method for the gas sensor element 100 of the present embodiment is a manufacturing method for the gas sensor element 100 including: the second insulating layer 142 including the pump cell 110 in which the first electrode 112 and the second electrode 113 are provided on the surface of the first solid electrolyte body 111; the first insulating layer 141 including the first measurement chamber R1 which is faced by the first electrode 112 and into which a gas to be measured flows; the second porous body 162 covering the second electrode 113; and the first dense layer 146A, the second dense layer 146B, and the third dense layer 146C having the atmospheric air introduction space 100G and not allowing the gas to be measured to pass therethrough, the second electrode 113 and the atmospheric air introduction space 100G being connected through the second porous body 162, the manufacturing method including a lamination step of forming the unfired laminate L which is the gas sensor element 100 before firing, and a firing step of firing the unfired laminate L to produce the gas sensor element 100, after the lamination step, wherein, in the gas sensor element 100, the first reinforcing layer 191 which is porous and contains, as a main component, a component having a lower sintering start temperature than the main component of the second porous body 162 is interposed between the second electrode 113 and the second porous body 162 at a position overlapping the atmospheric air introduction space 100G in the thickness direction of the second porous body 162, and the lamination step includes filling a region which becomes the atmospheric air introduction space 100G after firing, in the unfired dense layers 146AU and 146BU, with the vanishing paste Pd which varnishes due to firing, and forming the unfired reinforcing layer 191U between the unfired second electrode 113U and the unfired second porous body 162U.

The cracks around the first measurement chamber R1 are considered to be caused by the second insulating layer 142 warping so as to project toward the first measurement chamber R1 side during firing. Since the first reinforcing layer 191 which contains zirconia as a main component and has a lower shrinkage start temperature than the second porous body 162 is interposed between the second electrode 113 and the second porous body 162, and this first reinforcing layer 191 is caused to shrink earlier than the second porous body 162 during firing, the warp of the second insulating layer 142 can be alleviated, so that occurrence of cracks can be suppressed.

Also, the first reinforcing layer 191 is placed so as to overlap the measurement chamber arrangement region Ar in which the measurement chambers R1 and R2 are arranged, as viewed in the thickness direction of the first insulating layer 141.

In the second insulating layer 142, the portion overlapping the measurement chamber arrangement region Ar is likely to warp. Since the first reinforcing layer 191 is placed at the position overlapping the measurement chamber arrangement region Ar, occurrence of cracks due to the warp of the second insulating layer 142 can be more effectively suppressed.

The first reinforcing layer 191 has an outer shape larger than the measurement chamber arrangement region Ar, and overlaps the entire measurement chamber arrangement region Ar. With such a configuration, even if some misalignment of the first reinforcing layer 191 occurs during the manufacturing of the gas sensor element 100, the first reinforcing layer 191 can be reliably placed at the position overlapping the measurement chamber arrangement region Ar, so that occurrence of cracks can be suppressed.

Other Embodiments (1) In the above embodiment, the gas sensor is a NOx sensor for measuring nitrogen oxides in exhaust gas, but the type of gas sensor is not limited to that of the above embodiment, and may be, for example, an oxygen sensor for measuring the oxygen concentration of a gas to be measured. In addition, the gas to be measured is not limited to the exhaust gas, and various gases can be gases to be measured.

(2) In the above embodiment, the gas sensor element 100 has the first measurement chamber R1 and the second measurement chamber R2, but the number of measurement chambers provided in the gas sensor element is any number, and, for example, the gas sensor element may include one measurement chamber.

DESCRIPTION OF REFERENCE NUMERALS

1: gas sensor
20: terminal member
20A: element contact portion
100: gas sensor element
100G: atmospheric air introduction space (void)
100H: atmospheric air introduction port
110: pump cell
111: first solid electrolyte body (solid electrolyte body)
111U: unfired first solid electrolyte body (unfired solid electrolyte body)
112: first electrode
112U: unfired first electrode
113: second electrode
113U: unfired second electrode
121: second solid electrolyte body
121U: unfired second solid electrolyte body
122: third electrode
122U: unfired third electrode
123: fourth electrode
123U: unfired fourth electrode
131: third solid electrolyte body
131U: unfired third solid electrolyte body
132: fifth electrode
132U: unfired fifth electrode
133: sixth electrode
133U: unfired sixth electrode
141: first insulating layer (first ceramic layer)
141U: unfired first ceramic layer
142: second insulating layer (second ceramic layer)
142U: unfired second ceramic layer
143: third insulating layer
143U: unfired third ceramic layer
144: fourth insulating layer
144U: unfired fourth ceramic layer
145: fifth insulating layer
145U: unfired fifth ceramic layer
146A: first dense layer (dense layer)
146AU: unfired dense layer
146B: second dense layer (dense layer)
146BU: unfired dense layer
146C: third dense layer (dense layer)
151: first diffusion resistance body
151U: unfired first diffusion resistance body
152: second diffusion resistance body
152U: unfired second diffusion resistance body
161: first porous body
161U: unfired first porous body
162: second porous body (porous body)
162U: unfired second porous body (unfired porous body)
171: sixth insulating layer
172: seventh insulating layer
173: resistance heating element
181: alumina insulating layer
182: alumina insulating layer
182U: unfired insulating layer
183: alumina insulating layer
183U: unfired insulating layer
184: alumina insulating layer

184U: unfired insulating layer
191: first reinforcing layer (reinforcing layer)
191U: unfired reinforcing layer
Ar: measurement chamber arrangement region
H1: first through hole
H2: second through hole
H3: third through hole
H4: fourth through hole (space)
L: unfired laminate
Pd: vanishing paste (vanishing material)
R1: first measurement chamber (measurement chamber)
R2: second measurement chamber (measurement chamber)
R3: reference oxygen chamber
Ts: electrode terminal portion

What is claimed is:

1. A gas sensor element comprising:
a pump cell including a first surface, a second surface, a first electrode on the first surface, and a second electrode on the second surface;
a second ceramic layer including the pump cell;
a first ceramic layer defining a measurement chamber into which a gas to be measured flows, the first electrode facing the measurement chamber;
a porous body covering the second electrode, the porous body including, as a main component, a component having a sintering start temperature;
a dense layer defining a void and not allowing the gas to be measured to pass therethrough, the second electrode and the void connected through the porous body; and
a reinforcing layer which is porous and includes, as a main component, a component having a sintering start temperature, the sintering start temperature of the main component of the reinforcing layer being lower than the sintering start temperature of the main component of the porous body, the reinforcing layer interposed between the second electrode and the porous body at a position overlapping the void in a thickness direction of the porous body.

2. The gas sensor element according to claim 1, wherein the reinforcing layer includes zirconia as the main component.

3. The gas sensor element according to claim 1, further comprising a measurement chamber arrangement region in which the measurement chamber is arranged, wherein the reinforcing layer overlaps the measurement chamber arrangement region, as viewed in a thickness direction of the first ceramic layer.

4. The gas sensor element according to claim 3, wherein the measurement chamber arrangement region has an outer shape and the reinforcing layer has an outer shape, the outer shape of the reinforcing layer is larger than the outer shape of the measurement chamber arrangement region and entirely overlaps the outer shape of the measurement chamber arrangement region.

5. A gas sensor comprising the gas sensor element according to claim 1.

6. A manufacturing method for a gas sensor element, the gas sensor element including:
a pump cell including a first surface, a second surface, a first electrode on the first surface, and a second electrode on the second surface;
a second ceramic layer including the pump cell;
a first ceramic layer defining a measurement chamber into which a gas to be measured flows, the first electrode facing the measurement chamber;
a porous body covering the second electrode, the porous body including, as a main component, a component having a sintering start temperature; and
a dense layer defining a void and not allowing the gas to be measured to pass therethrough, the second electrode and the void being connected through the porous body,
the manufacturing method comprising:
a lamination step of forming an unfired laminate which is the gas sensor element before firing, and
a firing step of firing the unfired laminate to produce the gas sensor element, after the lamination step, wherein
in the gas sensor element, a reinforcing layer which is porous and includes, as a main component, a component having a sintering start temperature, the sintering start temperature of the main component of the reinforcing layer being lower than the sintering start temperature of the main component of the porous body, the reinforcing layer interposed between the second electrode and the porous body at a position overlapping the void in a thickness direction of the porous body, and
the lamination step includes:
filling a region in an unfired dense layer which becomes the void after firing, with a vanishing material which vanishes due to firing, and
forming an unfired reinforcing layer between an unfired second electrode and an unfired porous body.

* * * * *